United States Patent [19]

Nakao

[11] Patent Number: 5,318,520
[45] Date of Patent: Jun. 7, 1994

[54] SAFETY METHOD AND DEVICE FOR INTRAVENOUS FEED SYSTEMS

[76] Inventor: Naomi L. Nakao, 303 E. 57th St., New York, N.Y. 10022

[21] Appl. No.: 962,268

[22] Filed: Oct. 16, 1992

[51] Int. Cl.⁵ ............................................. A61M 31/00
[52] U.S. Cl. ..................................... 604/52; 604/122; 604/257; 604/262; 604/408
[58] Field of Search .................. 604/49, 53, 111, 122, 604/257, 262, 265, 404, 408, 80, 82-85, 52

[56] References Cited

U.S. PATENT DOCUMENTS

| | | | |
|---|---|---|---|
| 3,941,126 | 3/1976 | Dietrich et al. | 604/83 X |
| 4,792,333 | 12/1988 | Kidder | 604/83 |
| 4,981,468 | 1/1991 | Benefiel et al. | 604/83 |
| 5,030,215 | 7/1991 | Morse et al. | 604/410 |
| 5,069,671 | 12/1991 | Theeuwes | 604/251 |

Primary Examiner—C. Fred Rosenbaum
Assistant Examiner—Corrine Maglione
Attorney, Agent, or Firm—R. Neil Sudol; Henry D. Coleman

[57] ABSTRACT

A device for use in intravenous feeding comprises a reservoir of an intravenous fluid and an intravenous tube connected at one end to the reservoir, the tube being provided on an inner surface with a layer of a water-soluble biocompatible material visible through a wall of the tube. In use, an intravenous fluid is flushed through the tube or tube assembly until the water-soluble biocompatible layer dissolves and is no longer visible. Upon the dissolution of that layer into the intravenous fluid flowing through the tube assembly, a free end of the tube assembly is connected to a patient, while the tube assembly is maintained filled with the intravenous fluid.

13 Claims, 1 Drawing Sheet

SAFETY METHOD AND DEVICE FOR INTRAVENOUS FEED SYSTEMS

BACKGROUND OF THE INVENTION

This invention relates to a method and an associated device for use in intravenous feeding to improve the safety of the intravenous procedures. More particularly, this invention relates to a method and device for preventing the feeding of air intravenously to a patient.

In the feeding of fluids intravenously to a patient, care is usually taken to ensure that no air bubbles are present in the intravenous line prior to connection thereof to the patient. To remove air bubbles from the intravenous feed line, the line is flushed with the intravenous fluid or solution.

Despite the care that is normally taken to clear intravenous tubes of air bubbles, sometimes an intravenous line is not flushed for a sufficiently long period to ensure that all the air has been removed.

OBJECTS OF THE INVENTION

An object of the present invention is to provide a method for guarding against the feeding of air bubbles to a patient during an intravenous procedure.

Another object of the present invention is to provide a method which provides an alert indication to a nurse or doctor that an intravenous line may not have been sufficiently flushed with intravenous fluid to remove all of the residual air from the line.

Another, more particular, object of the present invention is to provide such a method which is easy and straightforward to execute.

An additional object of the present invention is to provide an intravenous feed device for guarding against the feeding of air bubbles to a patient during an intravenous procedure.

Another object of the present invention is to provide a device which provides an alert indication to a nurse or doctor that an intravenous line may not have been sufficiently flushed with intravenous fluid to remove all of the residual air from the line.

Another, more particular, object of the present invention is to provide such a device which is easy and straightforward to use.

These and other objects of the present invention will be apparent from the drawings and detailed descriptions herein.

SUMMARY OF THE INVENTION

A method for use in intravenous feeding comprises, in accordance with the present invention, the steps of (a) providing an intravenous tube assembly having on an inner surface a layer of water-soluble biocompatible material visible through a wall of the tube, (b) flushing an intravenous fluid through the tube assembly until the layer dissolves and is no longer visible, and (c) upon the dissolution of the layer into the intravenous fluid flowing through the tube assembly, connecting a free end of the tube to a patient, while maintaining the tube assembly filled with the intravenous fluid.

Where the tube assembly includes a flexible tube, the layer may be disposed on an inner surface of the tube. Alternatively, a separate connector piece at the free end of the tube (opposite the reservoir or bag of intravenous fluid) may be provided on an inner surface with the layer of water-soluble biocompatible material.

A device for use in intravenous feeding comprises, in accordance with the present invention, a reservoir of an intravenous fluid, and an intravenous tube connected at one end to the reservoir, the tube being provided on an inner surface with a layer of a water-soluble biocompatible material visible through a wall of the tube.

Pursuant to another feature of the present invention, the water-soluble biocompatible material has a predetermined color such as red. The material may be food coloring.

Pursuant to a further feature of the present invention, the dissolvable alert or indicator layer is cylindrical.

Pursuant to an additional feature of the present invention, the dissolvable alert or indicator layer has a predetermined thickness and density, whereby the layer dissolves upon the flushing of essentially a predetermined amount of fluid through the tube.

An intravenous line provided with an alert indicator in accordance with the present invention assures that the intravenous line will have been sufficiently flushed with intravenous fluid to remove residual bubbles in the line. The method is simple and straightforward and requires little or no education or practice to effectively follow.

DETAILED DESCRIPTION

Figure 1:
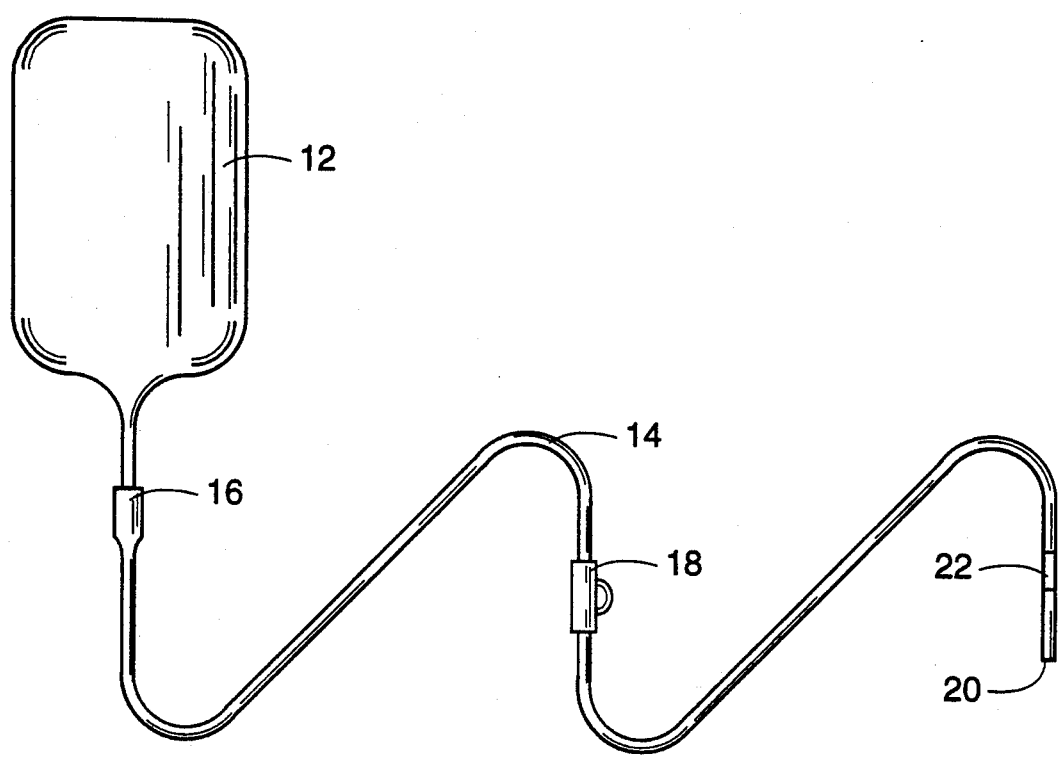
FIG. 1 is a schematic side elevational view of an intravenous feeding assembly in accordance with the present invention.
Figure 2:
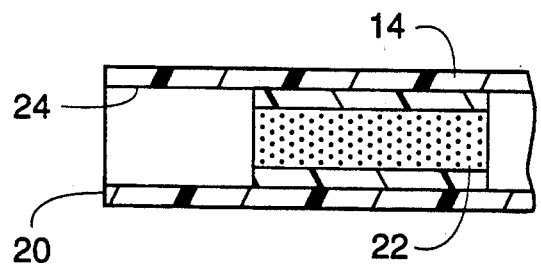
FIG. 2 is a partial cross-sectional view of a free end of an intravenous feed tube of the assembly of FIG. 1, showing a layer of water-soluble biocompatible material, on an enlarged scale, along an inner surface of the tube.

As illustrated in FIG. 1, an assembly or device for use in intravenous feeding comprises a flexible bag or reservoir 12 of an intravenous fluid and an intravenous tube 14 connected to one end of the reservoir via a drip chamber 16. A conventional roller type valve 18 is coupled to tube 14 for controlling the rate that intravenous fluid flows from reservoir 12 through tube 14. Tube 14 is provided at a predetermined location along its length, for example, at a free end 20 with a layer 22 of a water-soluble biocompatible material. Layer 22 is cylindrical and is deposited on an inner surface 24 of tube 14.

Layer 22 is visible through a wall of tube 14 for providing a visual indication as to whether a predetermined amount of fluid has flowed through tube 14 during a flushing operation. To that end, the water-soluble biocompatible material of layer 22 preferably has a readily sensed color such as red. The indicator material may be a food coloring and thus previously approved as biocompatible or ingestible by human beings.

The dissolvable alert or indicator layer 22 has a predetermined thickness and density, whereby the layer dissolves upon the flushing of essentially a predetermined amount of fluid through tube 14.

In use, an intravenous fluid is flushed through tube 14 until the water-soluble biocompatible layer 22 dissolves and is no longer visible. Upon the dissolution of layer 22 into the intravenous fluid flowing through tube 14, free end 20 of tube 14 is connected to a patient via a catheter (not shown). Upon the flushing of tube 14 and prior to the connection thereof to the patient, the tube is maintained filled with the intravenous fluid.

Figure 3:
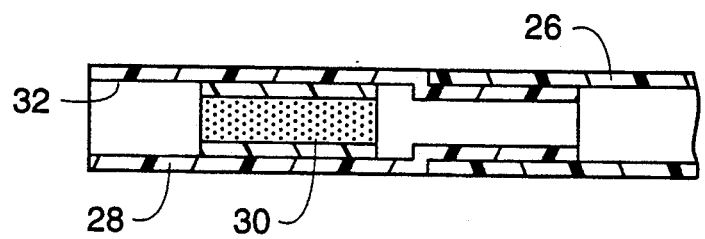
FIG. 3 is a partial cross-sectional view of a free end of an intravenous feed tube of another intravenous feeding assembly in accordance with the present invention, showing a layer of water-soluble biocompatible material, on an enlarged scale, along an inner surface of a connector element.

As illustrated in FIG. 3, a pre-existing intravenous tube 26 may be attached at a free end to a connector 28 which is in turn attachable to an intravenous catheter (not shown). Connector 28 is provided at a predetermined location with a layer 30 of a water-soluble biocompatible material. Layer 30 is preferably, although not necessarily, cylindrical and is deposited on an inner surface 32 of connector 28.

Layer 30 is visible through a wall (transparent) of connector 28 for providing a visual indication as to whether a predetermined amount of fluid has flowed through connector 28 during a flushing operation. Layer 30 has a readily sensed color such as red. The indicator material may be a food coloring and thus previously approved as biocompatible or ingestible by human beings.

Layer 30 has a predetermined thickness and density, whereby the layer dissolves upon the flushing of essentially a predetermined amount of fluid through connector 28.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in intravenous feeding, comprising the steps of:
providing an intravenous tube assembly including a reservoir of intravenous fluid and a tube extending from said reservoir, said tube assembly having, on an inner surface downstream of said reservoir, a layer of water-soluble biocompatible flow indicator material visible through a wall of said tube assembly;
flushing intravenous fluid from said reservoir through said tube until said layer substantially dissolves and essentially disappears; and
upon the dissolution of said layer into the intravenous fluid flowing through said tube, connecting a free end of said tube to a patient, while maintaining said tube filled with the intravenous fluid.

2. The method defined in claim 1 wherein said material has a color.

3. The method defined in claim 2 wherein said material is red.

4. The device defined in claim 1 wherein said material is food coloring.

5. The method defined in claim 1 wherein said layer is cylindrical.

6. The method defined in claim 1 wherein said layer is deposited on said tube.

7. The method defined in claim 1 wherein said tube assembly further includes a connector at a free end of said tube, said layer being disposed on said connector.

8. A device for use in intravenous feeding, comprising:
a reservoir of an intravenous fluid; and
an intravenous tubular member connected at one end to said reservoir, said tubular member being provided on an inner surface with a layer of water-soluble biocompatible material of a predetermined color visible through a wall of said tubular member.

9. The device defined in claim 8 wherein said material is red.

10. The device defined in claim 8 wherein said material is food coloring.

11. The device defined in claim 8 wherein said layer is cylindrical.

12. The device defined in claim 8 wherein said layer has a predetermined thickness and density, whereby said layer dissolves upon the flushing of essentially a predetermined amount of fluid through said tubular member.

13. A device for use in intravenous feeding, comprising:
a reservoir of an intravenous fluid; and
an intravenous tube connected at one end to said reservoir, said tube being provided on an inner surface with a cylindrical layer of a water-soluble biocompatible material visible through a wall of said tube.

* * * * *